US010570085B2

(12) United States Patent
Verkuijl et al.

(10) Patent No.: US 10,570,085 B2
(45) Date of Patent: Feb. 25, 2020

(54) PROCESS FOR MANUFACTURING ACRYLIC ACID

(71) Applicant: PURAC BIOCHEM B.V., Gorinchem (NL)

(72) Inventors: Bastiaan J. V. Verkuijl, Gorinchem (NL); Jan Van Krieken, Gorinchem (NL); Frédéric G. Terrade, Gorinchem (NL); Elisabeth Bouwman, Gorinchem (NL); Gijsbert Gerritsen, Gorinchem (NL); Jos Wilting, Gorinchem (NL)

(73) Assignee: PURAC BIOCHEM B.V., Gorinchen (NL)

( * ) Notice: Subject to any disclaimer, the term of this patent is extended or adjusted under 35 U.S.C. 154(b) by 0 days.

(21) Appl. No.: 16/063,435

(22) PCT Filed: Dec. 21, 2016

(86) PCT No.: PCT/EP2016/082076
§ 371 (c)(1),
(2) Date: Jun. 18, 2018

(87) PCT Pub. No.: WO2017/108890
PCT Pub. Date: Jun. 29, 2017

(65) Prior Publication Data
US 2018/0370895 A1    Dec. 27, 2018

(30) Foreign Application Priority Data
Dec. 21, 2015   (EP) ..................... 15201469

(51) Int. Cl.
*C07C 67/327*   (2006.01)
*C07C 57/04*    (2006.01)
*C07C 59/08*    (2006.01)
*C07C 51/09*    (2006.01)
*C07C 69/54*    (2006.01)
C07C 67/54     (2006.01)

(52) U.S. Cl.
CPC ............ *C07C 67/327* (2013.01); *C07C 51/09* (2013.01); *C07C 57/04* (2013.01); *C07C 59/08* (2013.01); *C07C 69/54* (2013.01); C07C 67/54 (2013.01)

(58) Field of Classification Search
CPC ....... C07C 57/04; C07C 51/09; C07C 67/327; C07C 69/54; C07C 59/08
See application file for complete search history.

(56) References Cited

U.S. PATENT DOCUMENTS

| | | | |
|---|---|---|---|
| 8,207,371 B2 | 6/2012 | Vogel et al. | |
| 2005/0222458 A1 | 10/2005 | Craciun et al. | |
| 2012/0078004 A1 | 3/2012 | Fruchey et al. | |

FOREIGN PATENT DOCUMENTS

| | | | | |
|---|---|---|---|---|
| WO | 2006/124899 A2 | 11/2006 | | |
| WO | WO 2006/124899 | * 11/2006 | ............. | C07B 41/12 |
| WO | 2013/134385 A1 | 9/2013 | | |
| WO | 2014/172540 A2 | 10/2014 | | |

OTHER PUBLICATIONS

Feb. 23, 2017 International Search Report issued in Patent Application No. PCT/EP2016/082076.
Feb. 23, 2017 Writen Opinion of the International Searching Authority issued in Patent Application No. PCT/EP2016/082076.

* cited by examiner

*Primary Examiner* — Yate' K Cutliff
(74) *Attorney, Agent, or Firm* — Oliff PLC

(57) ABSTRACT

Set forth is a process for preparing acrylic acid and/or the ester of acrylic acid and lactic acid from a lactic acid oligomer or polymer. As a result of the use of a bromide source and/or a chloride source in combination with a specific acid, a process that can be operated to obtain a high yield, and is relatively easy to perform, is realized.

31 Claims, No Drawings

PROCESS FOR MANUFACTURING ACRYLIC ACID

The present invention pertains to a process for manufacturing acrylic acid and related products.

Acrylic acid is a starting material for numerous materials. For example, acrylic acid is polymerized to form polyacrylic acid which finds use in diapers and other sanitary products, but also in applications like detergents, textiles and coatings. Methyl acrylate can be converted tho acrylic acid fibers suitable for use in textiles. Acrylic acid esters such as methyl acrylate, ethyl acrylate, and butyl acrylate and further acrylate esters find application in coatings, adhesives, inks, etc.

Traditionally, acrylic acid has been produced from propene which is a byproduct of ethylene and gasoline production. For environmental reasons there is a desire to manufacture acrylic acid from renewable resources. Further, with recent developments in gasoline production, less propylene is formed as side product, which has resulted in an increasing propylene price in recent years.

One possibility in this respect is lactide, which is the cyclic dimer of lactic acid. Lactic acid can be obtained by fermentation of renewable resources. Therewith, lactide is an attractive starting point for manufacturing acrylic acid. An advantage of using lactide as starting material is that the conversion into acrylic acid is a rearrangement reaction and does not require removal of water.

U.S. Pat. No. 8,207,371 describes a process for preparing a (meth)acrylic acid by converting a cyclic ester into (meth)acrylic acid in the presence of a catalyst, the catalyst being selected from alkali metal or alkaline metal salt of a carboxylic acid having 1 to 10 carbon atoms, a carbonate salt, a hydroxide, an oxide, a halogen salt or a sulfite salt. The document contains one example wherein tetramethyl glycolide is converted into methacrylic acid in the presence of the potassium salt of alpha-hydroxy butyric acid.

WO2006/124899 mentions the possibility of producing acrylic acid by contacting lactide with a catalyst which results in conversion of lactide to acrylic acid. The catalyst is described in very general terms as follows: "Suitable catalysts for the process include acidic catalyst, such as acidic inorganic and acidic organic compounds. Examples of the acidic catalyst include mineral acids, alumina, titania, silica, zirconia, silicates zeolites, aluminosilicate, acidic polymeric resins and the like. Useful mineral acids include acids such as sulfuric or phosphoric acid. Exemplary acidic resin catalysts include commercially available compounds such as NAFION™ resins (available from DuPont; Wilmington, Del.) and acidic DOWEX™ resins (available from Dow Chemical Co., Midland, Mich.). Suitable catalysts for the process include basic catalyst, such as basic inorganic and basic organic compounds. Examples of basic catalyst include metal hydroxides, metal oxides, amines and the like. Suitable catalysts for the process also include neutral compounds, such as metal phosphates, metal carboxylates, nitrates, sulfates, molybdates, and the like." The reference contains no examples whatsoever.

US2012/0078004 describes the conversion of lactide into acrylic acid by reacting lactide with acetic acid to form 2-acetoxy propionic acid in the presence of a catalyst, and then subjecting the 2-acetoxy propionic acid to a pyrolysis step to generate acrylic acid and acetic acid. This multi-step and energy-demanding process is not very attractive.

There is need in the art for a process which allows manufacture of acrylic acid from a lactic acid oligomer or polymer in high yield in an efficient manner. The present invention provides such a process.

It has been found that the process according to the invention also makes it possible to obtain the ester of acrylic acid and lactic acid in an efficient manner. This compound finds application in resins, coatings, adhesives, inks, etc.

The invention therefore pertains to a process for preparing acrylic acid and/or the ester of acrylic acid and lactic acid from a lactic acid oligomer or polymer, comprising the steps of bringing a reaction mixture comprising the lactic acid oligomer or polymer to reaction conditions to form acrylic acid and/or the ester of acrylic acid and lactic acid, the reacting mixture comprising a halide source selected from a bromide source and/or a chloride source and optionally an acid selected from the group of acids with a pKa of at most 2.0 and compounds which under reaction conditions decompose under the formation of an acid with a pKa of at most 2.0, with the reaction mixture comprising less than 1 wt. % of water, and keeping the reaction mixture under reaction conditions for a time sufficient to produce acrylic acid and/or the ester of acrylic acid and lactic acid.

It has been found that the use of a bromide source and/or a chloride source optionally in combination with the specified acid results in a process which can be operated to obtain a high yield, and is relatively easy to perform. One advantage of the process according to the invention is that it can be carried out in the liquid phase, using a relatively inexpensive homogeneous catalyst. Further advantages of the process according to the invention and specific embodiments thereof will become clear from the further specification.

The process according to the invention may be conducted with or without the addition of an acid selected from the group of acids with a pKa of at most 2.0 and compounds which under reaction conditions decompose under the formation of an acid with a pKa of at most 2.0. It was found that when no additional acid is added in general the yield of acrylic acid is lower, but a different product distribution is obtained. For instance less by-products are obtained which result in acrylic acid of higher purity.

In an embodiment of the invention the process is conducted without the addition of an acid selected from the group of acids with a pKa of at most 2.0 and compounds which under reaction conditions decompose under the formation of an acid with a pKa of at most 2.0, with the reaction mixture comprising less than 1 wt. % of water. It was found that in this embodiment the amount of 3-bromopropionic acid could be kept below 11% of the amount of acrylic acid formed. The amount of 2-bromopropionic acid could be kept below 5% of the amount of acrylic acid formed.

Preferably such a process is conducted using magnesium bromide and/or aluminium bromide as a halide source, since with these catalysts relatively low amounts of 2-bromopropionic acid (2BrPA) and 3-bromopropionic acid (3BrPA) were formed, while showing good acrylic acid yields. When using magnesium bromide and/or aluminium bromide as a halide source, acrylic acid yields of above 30% could be obtained while the amounts of 2-bromopropionic acid could be kept below 3% of the amount of acrylic acid formed and the amount of 3-bromopropionic acid could be kept below 11% of the amount of acrylic acid formed.

With the addition of an acid selected from the group of acids with a pKa of at most 2.0 and compounds which under reaction conditions decompose under the formation of an acid with a pKa of at most 2.0, a higher yield of acrylic acid may be obtained.

The present invention is suitable for the conversion of a lactic acid oligomer or polymer. Suitable starting materials thus include lactide, which is a cyclic lactic acid dimer, other lactic acid oligomers than lactide, and polylactic acid. Within the context of the present specification the term lactide refers to the cyclic dimer of lactic acid, the term other lactic acid oligomers (or oligolactic acid) refers to lactic acid oligomers other than lactide with a number average molecular weight which is at least that of lactide and below 3000 g/mol, and the term polylactic acid (PLA) refers to a lactic acid polymer with a molecular weight of at least 3000 g/mole. As upper limit of the molecular weight of PLA a value of 1.000.000 g/mole may be mentioned.

Lactide, other lactic acid oligomers than lactide, and PLA are commercially available and require no further elucidation here. The material can be virgin or waste material. Especially for PLA the use of waste material may be an attractive option.

In the process according to the invention a bromide source and/or a chloride source is used. It is possible to use either a bromide source or a chloride source, but a combination of the two is also possible. Of course it is possible to use one type of bromide or chloride source, but mixtures of various sources are also possible. In the following, the bromide or chloride source may also be indicated as halide source.

In general, a bromide source may be preferred from an activity point of view, while a chloride source may be attractive from an availability point of view.

The halide source in the present invention may be an organic or inorganic halide source.

Examples of inorganic halide sources are acids or inorganic salts. Examples include KBr, NaBr, CuBr, $FeBr_2$, $FeBr_3$, $NiBr_2$, LiBr, $MgBr_2$, $AlBr_3$, and $ZnBr_2$.

The organic halide source preferably is an organic halide salt, in particular a salt comprising a positively charged phosphorus or nitrogen atom and a negatively charged chloride or bromide ion.

Examples of suitable halide salts are as follows:
organophosphonium halide salts of the formula R1R2R3R4PX, wherein X is Cl or Br, and R1, R2, R3, and R4 are independently selected from alkyl, aryl, arylalkyl, and alkylaryl with 1-10 carbon atoms, in particular phenyl or alkyl, e.g., tetraphenylphosphonium bromide and tetrabutyl phosphonium bromide.
imididazolium halides wherein at least one nitrogen atom, and preferably both nitrogen atoms in the imidazolium ring are substituted with substituents R1 and R2 which are independently selected from alkyl, aryl, arylalkyl, and alkylaryl with 1-10 carbon atoms, in particular C1-C4 alkyl, e.g., 1-ethyl-3-methyl imidazolium bromide.
pyridinium halide salts, wherein the nitrogen atom in the pyridinium ring is substituted with R1 which is selected from alkyl, aryl, arylalkyl, and alkylaryl with 1-10 carbon atoms, in particular C1-C4 alkyl, e.g., 1-butyl pyridinium bromide or 1-butyl pyridinium chloride.

The pyridinium ring and imidazolium ring of the salts described above may optionally also be substituted with alkyl, aryl, arylalkyl, and alkylaryl with 1-10 carbon atoms.

Organo-ammonium halide salts can also be used, e.g., compounds of the formula R1R2R3R4NX, wherein X is Cl or Br, and R1, R2, R3, and R4 are independently selected from alkyl, aryl, arylalkyl, and alkylaryl with 1-10 carbon atoms, in particular phenyl or alkyl, e.g., tetrabutylammonium bromide. The use of pyrrolidinium halide salts is also envisaged, as is the use of other onium halides such as alkyl arsonium bromide or chloride, e.g., tetramethyl arsonium bromide or tetraethyl arsonium bromide, or the corresponding chlorides.

Combinations of various types of halide sources can of course also be used.

In one embodiment of the present invention an iodide compound is used in addition to a chloride or bromide.

As mentioned above, in the present invention an acid may be used which is selected from the group of acids with a pKa of at most 2.0 or a compound which under reaction conditions decomposes under the formation of an acid with a pKa of at most 2.0.

If an acid is used, it is preferred to use an acid with a pKa of at most 1.5, in particular at most 1.0. Suitable acids encompass both organic acids and inorganic acids. Suitable inorganic acids include HBr, HCl, $HNO_3$, $H_2SO_4$, $H_3PO_3$, and $H_3PO_4$. Where the acid is HBr or HCl, the compound can act both as bromide source and as acid. An issue with the inorganic acids is that the reaction mixture is to comprise less than 1 wt. % of water. It may be difficult to provide these inorganic acids at such a low water content. Therefore, organic acids with a pKa of at most 2.0, in particular at most 1.5, more in particular at most 1.0 are considered preferred. Examples of such acids include methane sulfonic acid, para-toluene sulfonic acid, and trifluoroacetic acid.

If a compound is used which under reaction conditions decomposes under the formation of an acid, it is preferred for the resulting acid to have a pKa of at most 1.5, in particular at most 1.0. Suitable compounds of this type include 2-bromopropionic acid and 3-bromopropionic acid which under reaction conditions decompose to form HBr and acrylic acid.

The reaction mixture in the process according to the invention comprises less than 1 wt. % of water. This is because the presence of water results in hydrolysis of the lactide or PLA starting material, and therewith detrimentally affects the yield of the process. It is preferred for the water content of the reaction mixture to be below 0.5 wt. %, in particular below 0.1 wt. %. As will be evident to the skilled person, the water content can be regulated by controlling the water present in the starting components and by limiting the amount of water entering the system through other means.

The ratio between the various components may vary within wide ranges.

If the amount of lactide (or other lactic acid oligomer or PLA expressed as lactide) is set at 1, the amount of halogen source can vary between 10 and 0.1. In other words: the molar ratio between the halogen source and lactide may range from 10:1 to 0.1:1. When a very large amount of halogen source is used, it will act partially as reactant and partially as solvent. Where only a limited amount of halogen source is used, the reaction rate may be quite low. It may therefore be preferred for the molar ratio between halogen source and lactide to range from 10:1 to 0.5:1.

The molar ratio between the acid and the lactide generally ranges from 0.01:1 to 1:1. When the amount of acid is very low, the reaction rate may be too low for attractive commercial operation. When the amount of acid is high, the reaction rate may not be improved further or even lowered. It may be preferred for the molar ratio between the acid and the lactide to range from 0.1:1 to 0.5:1. It was found that an optimal acrylic acid yield may be obtained at a molar ratio of between 0.3:1 to 0.6:1.

In the above, the ratios are expressed on the amount of lactide. If oligolactic acid or polylactic acid is used as starting material, the molar ratios should be calculated to the equivalent amount of lactide. This can be done by multiplying the number of moles of oligolactic acid or PLA with the average molecular weight of the oligolactic acid or PLA, and dividing this figure by the molecular weight of lactide (144).

The reaction mixture can further comprise a solvent. The advantage of a solvent is that it can increase the reaction rate by dissolving the solid starting lactic acid oligomer or polymer therein. The solvent should meet the following requirements: the starting lactic acid oligomer or polymer, halide source, and acid should be soluble in the solvent and the solvent should not negatively affect the reaction, e.g. by reacting with the starting materials, intermediates, or reaction products. Suitable solvents are generally selected from the group of polar aprotic solvents, including, e.g., sulfolane, dichloromethane, tetrahydrofuran, acetonitrile, dimethylformamide, dimethyl sulfoxide, and acetone. It is within the scope of the skilled person to select a suitable solvent.

The amount of solvent will be governed by the following general considerations. The minimum amount will be governed by the amount required to obtain a reaction mixture wherein the various components are dissolved and which has a suitable viscosity under reaction conditions. The maximum amount will be determined by the amount at which the reaction rate decreases, as a result of the dilution of the reaction mixture being too high. In general, the amount of solvent, if used, will comprise 10-90 wt. % of the reaction mixture.

The reaction conditions for the process according to the invention may be selected within wide ranges.

The reaction temperature is generally at least 20° C., more in particular at least 50° C., still more in particular at least 100° C. Higher reaction temperatures generally lead to a higher reaction rate. A too high reaction temperature may lead to the formation of side-product and unnecessary energy consumption. The reaction temperature will generally be at most 400° C., in particular at most 300° C., more in particular at most 250° C. A reaction temperature between 125 and 225° C. may be particularly preferred.

The reaction pressure is not critical to the process according to the invention. It has been found that the reaction can be performed at high pressure, e.g., in the range of 10-100 bar. On the other hand, good results have also been obtained at atmospheric pressure or at a pressure slightly above atmospheric pressure, e.g., in the range of 1-10 bar. Operation at a pressure in the range of 1-5 bar may be preferred for reasons of process economy. On the other hand, operation at a pressure below 1 bar may be attractive to effect removal of the acrylic acid. In this embodiment it may be preferred for the pressure to be below 0.1 bar.

The reaction time may vary within wide ranges, depending on, int. al., the reaction temperature, the type and amount of halogen source and the type and amount of acid. In general, the reaction time will be at least 15 minutes, in particular at least 30 minutes. Longer reaction times lead to a higher yield of acrylic acid. Therefore, it may be preferred for the reaction time to be at least 1 hour, in particular at least 2 hours. Reaction times longer than 48 hours are generally avoided, since they are not attractive form an economic point of view. It is preferred for the reaction time to be at most 24 hours, in particular at most 20 hours.

The process according to the invention yields acrylic acid and/or the ester of acrylic acid with lactic acid, depending on the reaction conditions. As the ester of acrylic acid with lactic acid is an intermediate product, it is believed that conditions which favour conversion will also favour the production of acrylic acid rather than the ester of acrylic acid with lactic acid. These conditions include higher reaction temperatures and longer reaction times. It is within the scope of the skilled person to select reaction conditions which maximise the yield of the desired product.

The process can be carried out in batch mode or in a continuous mode. From a processing point of view, a continuous process is considered preferred. In a continuous process the residence time is a balance between sufficient time to carry out the reaction to an appropriate yield and avoiding needless occupation of the unit. It is within the scope of the skilled person to select a suitable residence time.

In the process according to the invention, a reaction mixture comprising the starting components, halide source and acid are brought to reaction conditions, and the mixture is allowed to react until the desired amount of product acrylic acid and/or ester of acrylic acid with lactic acid is obtained.

It is within the scope of the skilled person to determine how this should be carried out, and this requires no further elucidation.

The acrylic acid and/or the ester of acrylic acid with lactic acid is generally recovered from the reaction mixture during or after the reaction. This can be done, e.g., through distillation or via extraction.

In one embodiment the process according to the invention is carried out in the form of a reactive distillation process. In this embodiment the process according to the invention is carried out under such conditions of temperature and pressure that the acrylic acid formed during the reaction is distilled from the reaction mixture during the reaction. This embodiment is particularly attractive where the reaction is aimed at the production of acrylic acid.

The present invention is illustrated by the following examples, without being limited thereto or thereby.

EXAMPLE 1

2 mmole of (S,S)-lactide, a bromide source, and methane sulfonic acid were placed in a glass jar insert equipped with a stirring bar which was introduced in an autoclave. The molar ratio between the bromide source and the methane sulfonic acid was 6:1. The molar ratio of the bromide source to lactide was 5:1. Sulfolane was used as a solvent in an amount of 1 ml per gram of bromide source. The autoclave was closed and pressurized with 50 bar $N_2$, and heated using a heating mantle under stirring to the required temperature for 16 hours reaction time. When the reaction was completed, the autoclave was placed in an ice bath for 10-30 minutes, before being vented and opened. The products were analysed using 1H-NMR. The bromide source was tetraphenyl phosphonium bromide (PPh4Br) or tetrabutylammonium bromide (TBAB). Results are presented in Table 1 below. In all cases the conversion was 100%. Yield is the molar yield expressed as a percentage of the starting lactide.

In the Table, AA stands for acrylic acid. C2 or Compound 2 stands for the ester of acrylic acid with lactic acid with the following formula:

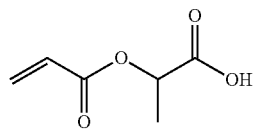

C2

Esters stands for the group of compounds with the following formula's.

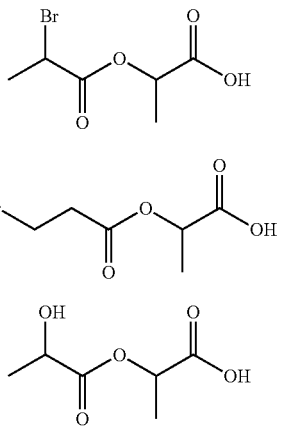

E1
E2
E3

Compound 2, while an ester, is thus not encompassed in this group. 2BrPA stands for 2-bromopropionic acid. 3BrPA stands for 3-bromopropionic acid. m.b. stands for the mass balance.

TABLE 1

| exp | Br-source | T (° C.) | Yield AA | Yield C2 | Yield esters | Yield 2BrPA | Yield 3BrPA | m.b. |
|---|---|---|---|---|---|---|---|---|
| 1.1 | PPh4Br | 150 | 32 | 44 | 4 | 6 | 7 | 93 |
| 1.2 | PPh4Br | 175 | 52 | 3 | 0 | 0 | 4 | 59 |
| 1.3 | PPh4Br | 200 | 2 | 0 | 0 | 0 | 0 | 2 |
| 1.4 | TBAB | 150 | 18 | 44 | 22 | 8 | 1 | 92 |
| 1.5 | TBAB | 175 | 31 | 14 | 5 | 2 | 5 | 58 |
| 1.6 | TBAB | 200 | 28 | 0 | 0 | 0 | 4 | 32 |

From Table 1 it can be seen that increasing the reaction temperature leads to increased formation of acrylic acid and an increased selectivity to acrylic acid rather than Compound 2 or other esters. If the reaction temperature becomes too high, other products are obtained, not specified in the table. In the present circumstances in Example 1.3 a small amount of AA was obtained. However, it was possible to obtain higher amounts of AA at this temperature when selecting a different bromide source or ratio between the various components.

EXAMPLE 2

In this example, the production of AA was followed over time. The reaction was carried out as described in Example 1, with PPh4Br as the bromide source at a temperature of 175° C. The molar ratio between the bromide source and methane sulfonic acid was 6:1. The molar ratio of the bromide source to lactide was 5:1. Results are presented in Table 2. Conv. stands for lactide conversion in %.

TABLE 2

| exp | t(h) | Conv | Yield AA | Yield C2 | Yield esters | Yield 2BrPA | Yield 3BrPA | m.b. |
|---|---|---|---|---|---|---|---|---|
| 2.1 | 1 | 83 | 10 | 40 | 20 | 11 | 1 | 100 |
| 2.2 | 2 | 94 | 17 | 47 | 15 | 10 | 2 | 97 |
| 2.3 | 4 | 100 | 42 | 40 | 2 | 6 | 6 | 96 |
| 2.4 | 6 | 100 | 46 | 35 | 2 | 4 | 7 | 93 |
| 2.5 | 8 | 100 | 54 | 15 | 0 | 2 | 6 | 76 |
| 2.6 | 10 | 100 | 58 | 12 | 2 | 0 | 5 | 76 |

The results indicate that a longer reaction time leads to increased formation of AA.

EXAMPLE 3

In this example the effect of the use of various inorganic bromide sources is investigated. The reaction was carried out as follows: 400 mg (2.78 mmol) lactide, 0.28 mmol MBrx, 5.80 g (13.8 mmol) tetraphenylphosphonium bromide, 222 mg (150 µl, 2.31 mmol) methane sulfonic acid, and 7.50 g (6 mL, 62.4 mmol) sulfolane were added to a reaction flask with magnetic stirring bar and heated to 175° C. (temperature of oil bath) while connected to an atmospheric nitrogen line. Samples were taken after 20 h. The results are presented in Table 3.

TABLE 3 various inorganic Bromide sources

| exp | Br-source | Yield AA | Yield C2 | Yield esters | Yield 2BrPA | Yield 3BrPA | m.b. |
|---|---|---|---|---|---|---|---|
| 3.1 | CuBr | 43.5 | 1.1 | 0.0 | 0.5 | 3.6 | 50.6 |
| 3.2 | FeBr3 | 41.2 | 0.9 | 0.0 | 0.5 | 4.4 | 56.5 |
| 3.3 | NiBr2 | 49.8 | 1.4 | 0.0 | 0.6 | 6.2 | 60.4 |
| 3.4 | LiBr | 48.4 | 1.0 | 0.0 | 0.5 | 6.7 | 58.7 |
| 3.5 | MgBr2 | 46.4 | 0.8 | 0.0 | 0.6 | 8.2 | 57.6 |
| 3.6 | AlBr3 | 36.4 | 0.0 | 0.0 | 0.8 | 11.2 | 50.7 |
| 3.7 | FeBr2 | 32.7 | 0.8 | 0.0 | 0.4 | 4.8 | 61.7 |
| 3.8 | ZnBr2 | 48.2 | 0.9 | 0.0 | 0.5 | 5.8 | 57.3 |

EXAMPLE 4

In this example the effect of the use of various bromide sources is investigated without using an additional Brønsted acid. The reaction was carried out as follows: 400 mg (2.78 mmol) lactide, 0.28 mmol MBrx, 5.80 g (13.8 mmol) tetraphenylphosphonium bromide, and 7.50 g (6 mL, 62.4 mmol) sulfolane were added to a reaction flask with magnetic stirring bar and heated to 175° C. (temperature of oil bath) while connected to an atmospheric nitrogen line. Samples were taken after 20 h. The results are presented in Table 4.

TABLE 4 various bromide sources without additional acid

| exp | Br-source | Yield AA | Yield C2 | Yield esters | Yield 2BrPA | Yield 3BrPA | m.b. |
|---|---|---|---|---|---|---|---|
| 4.1 | CuBr | 8.6 | 6.9 | 10.6 | 0.4 | 0.0 | 77.8 |
| 4.2 | FeBr3 | 29.6 | 4.4 | 0.5 | 0.5 | 0.6 | 66.3 |
| 4.3 | NiBr2 | 7.0 | 5.0 | 8.9 | 0.3 | 0.0 | 60.7 |
| 4.4 | LiBr | 9.9 | 7.6 | 9.7 | 0.4 | 0.0 | 61.1 |
| 4.5 | MgBr2 | 46.9 | 3.6 | 0.8 | 0.3 | 0.2 | 58.3 |
| 4.6 | AlBr3 | 39.2 | 0.4 | 0.0 | 0.5 | 4.2 | 48.0 |
| 4.7 | FeBr2 | 2.3 | 1.1 | 7.9 | 0.3 | 0.0 | 53.8 |
| 4.8 | ZnBr2 | 7.9 | 6.3 | 9.1 | 0.4 | 0.0 | 62.7 |

These results show that, although in general the acrylic acid yields are lower in the absence of an additional acid, good acrylic acid yields can be obtained with various bromide sources in the absence of an additional acid. For instance, magnesium bromide and aluminium bromide show good acrylic acid yields, while relatively low amounts of 2-bromopropionic acid (2BrPA) and 3-bromopropionic acid (3BrPA) was formed, when compared to a process with the same bromide source using an additional acid (See experiment 3.5 and 3.6).

EXAMPLE 5

In this example the effect of the amount of methane sulfonic acid used in the system, is investigated. The tests were carried out as described for Example 3, using 0, 40, 80, and 160 mole % of methane sulfonic acid, respectively, and magnesium bromide as the bromide source. Samples are taken after 20 h. The results have been compiled in Table 5.

TABLE 5 various amounts of methyl sulfonic acid

| exp | Methyl sulfonic acid (Mole %) | Yield AA | Yield C2 | Yield esters | Yield 2BrPA | Yield 3BrPA | m.b. |
|---|---|---|---|---|---|---|---|
| 5.1 | 0 | 46.9 | 3.6 | 0.8 | 0.3 | 0.2 | 58.3 |
| 5.2 | 40 | 54.7 | 2.6 | 0.0 | 0.5 | 3.0 | 63.5 |
| 5.3 | 80 | 46.4 | 0.8 | 0.0 | 0.6 | 8.2 | 57.6 |
| 5.4 | 160 | 46.2 | 0.8 | 0.6 | 0.8 | 10.3 | 59.6 |

These results show that the optimal amount of additional acid was about 40 mole %.

EXAMPLE 6

In this example the effect of adding 2-bromopropionic acid (2BrPA) or 3-bromopropionic acid (3BrPA) to the system was investigated. Under reaction conditions these compounds decompose into acrylic acid and HBr, which acts as strong acid. The tests were carried out as described for Example 1. Reaction temperature was 150° C., reaction time was 16 hours. Ratio between bromide source and lactide was 5:1. Reaction pressure was 50 bar. The results are presented in Table 6a for TBAB as bromide source and Table 6b for PPh4Br as bromide source. The amount of BrPA added is expressed as equivalents calculated on the amount of lactide.

TABLE 6a

TBAB as bromide source

| exp | BrPA (eq) | Conv | Yield AA | Yield C2 | Yield esters | Yield 2BrPA | Yield 3BrPA | m.b. |
|---|---|---|---|---|---|---|---|---|
| 6.1 | 2BrPa (0.1) | 39 | 0 | 4 | 45 | 0 | 0 | 111 |
| 6.2 | 2BrPa (0.5) | 75 | 11 | 32 | 40 | 3 | 0 | 110 |
| 6.3 | 2BrPa (1.0) | 99 | 27 | 40 | 17 | 14 | 6 | 106 |

TABLE 6b

PPh4Br as bromide source

| exp | BrPA (eq) | Conv | Yield AA | Yield C2 | Yield esters | Yield 2BrPA | Yield 3BrPA | m.b. |
|---|---|---|---|---|---|---|---|---|
| 6.4 | 2BrPa (0.1) | 61 | 10 | 24 | 15 | 3 | 0 | 91 |
| 6.5 | 2BrPa (0.5) | 100 | 31 | 35 | 7 | 6 | 10 | 90 |
| 6.6 | 2BrPa (1.0) | 100 | 27 | 28 | 9 | 10 | 19 | 93 |
| 6.7 | 3BrPa (0.5) | 100 | 35 | 35 | 6 | 6 | 10 | 94 |
| 6.8 | 3BrPa (1.0) | 100 | 39 | 21 | 7 | 6 | 21 | 94 |

The results in Tables 6a and 6b show that the use of 2BrPA and 3BrPA give good results in the manufacture of acrylic acid from lactide.

EXAMPLE 7

The effect of different types of acids was investigated. The tests are carried out as described for Example 1. Reaction temperature was 150° C., reaction time was 16 hours. Ratio between bromide source and lactide was 5:1. The bromide source was PPh4Br. Reaction pressure was 50 bar. Sulfolane was used as a solvent in an amount of 1 ml per gram of bromide source. The results are presented in Table 7. The amount of acid is expressed as equivalents calculated on lactide. TFA stands for trifluoroacetic acid. LA stands for lactic acid.

TABLE 7 different types of acids

| exp | acid (eq) | Conv | Yield AA | Yield C2 | Yield LA | Yield Esters | Yield 2BrPA | Yield 3BrPA | m.b. |
|---|---|---|---|---|---|---|---|---|---|
| 7.1 | TFA (0.5) | 54 | 5 | 16 | 0 | 8 | 0 | 0 | 75 |
| 7.2 | TFA (1.0) | 78 | 10 | 29 | 0 | 17 | 3 | 0 | 80 |
| 7.3 | oxalic (0.5) | 61 | 0 | 0 | 10 | 37 | 0 | 0 | 85 |
| 7.4 | oxalic (1.0) | 76 | 0 | 0 | 21 | 41 | 0 | 0 | 86 |
| 7.5 | $H_3PO_3$ (0.5) | 66 | 11 | 33 | 0 | 7 | 8 | 0 | 93 |
| 7.6 | $H_3PO_3$ (1.0) | 97 | 23 | 49 | 0 | 1 | 7 | 2 | 85 |
| 7.7 | acetic (0.5) | 32 | 0 | 0 | 3 | 10 | 0 | 0 | 81 |
| 7.8 | acetic (1.0) | 32 | 0 | 0 | 2 | 10 | 0 | 0 | 80 |

From Table 7 it can be seen that the strong acids (pKa below 2.0) trifluoroacetic acid and phosphonic acid result in the formation of acrylic acid under the conditions of this experiment, while oxalic acid and acetic acid do not.

EXAMPLE 8

In this experiment the influence of the presence of solvent was investigated. The tests were carried out as described for Example 1. Reaction temperature was 150° C., reaction time was 16 hours. Ratio between bromide source and lactide was 5:1. The bromide source was PPh4Br. Reaction pressure was 50 bar. Sulfolane was used as a solvent. The results are presented in Table 5. The amount of solvent is expressed as the volume of sulfolane in ml divided by the mass of the PPh4Br in gram.

TABLE 8

| exp | solvent (ml/g) | Conv | Yield AA | Yield C2 | Yield Esters | Yield 2BrPA | Yield 3BrPA | m.b. |
|---|---|---|---|---|---|---|---|---|
| 8.1 | 0.3 | 98 | 15 | 42 | 28 | 9 | 5 | 101 |
| 8.2 | 0.7 | 100 | 27 | 45 | 7 | 6 | 7 | 92 |
| 8.3 | 1.0 | 100 | 32 | 44 | 4 | 6 | 7 | 93 |
| 8.4 | 1.4 | 99 | 26 | 43 | 9 | 7 | 4 | 89 |
| 8.5 | 1.7 | 93 | 18 | 42 | 13 | 11 | 3 | 94 |

EXAMPLE 9

In this example the effectiveness of using a chloride source was investigated. The test was carried out as described for Example 1. Reaction temperature was 150° C., reaction time was 16 hours. The chloride source was tetraphenyl phosphonium chloride (PPh4Cl). The ratio between the chloride source and lactide was 5:1. Reaction pressure was 50 bar. Sulfolane was used as a solvent in an amount of 1 ml per gram of PPh4Cl. The result is presented in Table 9.

TABLE 9

| exp | Conv | Yield AA | Yield 2 | Yield esters* | Yield 2ClPA | m.b. |
|---|---|---|---|---|---|---|
| 9.1 | 86 | 9 | 25 | 26 | 23 | 96 |

From this example it can be seen that the use of a chloride source also yields acrylic acid and the ester of acrylic acid with lactic acid.

EXAMPLE 10

In this example the use of oligolactic acid and polylactic acid as starting material was investigated. The properties of the starting material are presented in Table 10a.

Eq of HOMs relative to LA units stands for (the quantity of methane sulfonic acid in mmol divided by the quantity of polymer or oligomer in mmol) multiplied by the degree of polymerization.

The average number of LA units per molecule in the oligolactide was determined using NMR. Two types of PLA were used, namely a commercially available fresh PLA and a PLA in the form of compostable cutlery TABLE 10a

| substrate | molecular weight (g/mol) | average number of LA units per molecule | number of mmol LA units in 100 mg substrate | eq of HOMs relative to LA units |
|---|---|---|---|---|
| lactide | 144.13 | 2 | 1.39 | 0.42 |
| oligolactic acid | 853.2 | 11.6 | 1.36 | 0.43 |
| PLA | >>853.2 | >>11.6 | 1.39 | 0.42 |
| PLA knife | >>853.2 | >>11.6 | 1.39 | 0.42 |

The various substrates were processed as follows: 100 mg of substrate, 0.58 mmol of methane sulfonic acid, 3.47 mmol of tetraphenylphosphonium bromide and 1.5 ml of sulfolane were placed in a glass jar inset equipped with a stirring bar which was introduced in an autoclave. The ratio of the bromide source to lactide units was 2.5-2.6 in all experiments. The autoclave was closed and pressurized with 50 bar $N_2$, and heated using a heating mantle under stirring to a temperature of 150° C. for 16 hours reaction time. When the reaction was completed, the autoclave was placed in an ice bath for 30 minutes, before being vented and opened. The results are presented in Table 10b.

TABLE 10b

| exp | substrate | Conv | Yield AA | Yield C2 | Yield C3 | Yield LA | Yield oligo | Yield 2BrPA | Yield 3BrPA | m.b. |
|---|---|---|---|---|---|---|---|---|---|---|
| 10.1 | lactide | 100 | 32 | 44 | 0 | 0 | 26 | 6 | 7 | 93 |
| 10.2 | oligo-LA | / | 23 | 27 | 11 | 7 | 27 | 7 | 4 | 87 |
| 10.3 | PLA | / | 24 | 26 | 16 | 5 | 32 | 8 | 5 | 93 |
| 10.4 | recycle PLA | / | 25 | 26 | 15 | 3 | 30 | 6 | 5 | 86 |

In Table 10b, / stands for not determined. C2 and C3 stand for the following compounds. C2 is the ester of acrylic acid with lactic acid. C3 is the ester of acrylic acid with a lactic acid dimer.

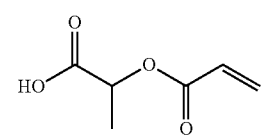

C2

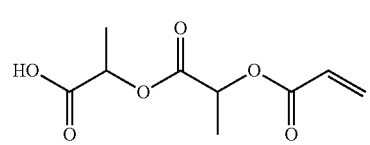

C3

From Table 10b it can be seen that not only lactide but also oligolactic acid and polylactic acid can serve as starting material in the production of acrylic acid and the ester of acrylic acid with lactic acid via the process according to the invention.

EXAMPLE 11

In this experiment the effect of pressure conditions was investigated. In the experiments in the autoclave 0.69 mmole of lactide (100 mg), 0.58 mmole of methane sulfonic acid, 3.47 mmole of tetraphenylphosphonium bromide (1.49 g), and 1.5 ml sulfolane were used. For the reactions in the Schlenk reactor and the flasks, the amounts were doubled. The results are presented in Table 11.

TABLE 11

| exp | set-up | t (h) | T (° C.) | P (bar) | Yield AA | Yield C2 | Yield oligo | Yield 2BrPA | Yield 3BrPA | m.b. |
|---|---|---|---|---|---|---|---|---|---|---|
| 11.1 | autoclave | 16 | 150 | 50 | 32 | 44 | 26 | 6 | 7 | 93 |
| 11.2 | autoclave | 16 | 150 | <5 | 35 | 39 | 25 | 5 | 6 | 90 |
| 11.3 | autoclave | 4 | 175 | 50 | 42 | 40 | 22 | 6 | 6 | 96 |
| 11.4 | autoclave | 6 | 175 | 50 | 46 | 35 | 19 | 4 | 7 | 93 |
| 11.5 | autoclave | 10 | 175 | 50 | 58 | 12 | 8 | 0 | 5 | 76 |
| 11.6 | Schlenk | 5 | 175 | atm | 58 | 25 | 15 | 4 | 7 | 97 |
| 11.7 | reactor flask | 3 | 175 | atm | 38 | 42 | 24 | 5 | 7 | 95 |

In the autoclave the pressure of 50 bar is obtained by bringing the autoclave to the indicated pressure at room temperature. At reaction temperature the pressure was above 60 bar. In Example 8.2, the autoclave was not pressurised. It was closed at room temperature and heated to the reaction temperature. The pressure in the autoclave at reaction temperature was about 3 bar. In the Schlenk reactor and in the reactor flask, the pressure was atmospheric. This example shows that the pressure is not critical to obtaining acrylic acid.

EXAMPLE 12

In this example manufacturing acrylic acid from lactide in a reactive distillation set up was investigated as follows: 400 mg lactide (2.78 mmol), 150.2 microliter methane sulfonic acid (2.31 mmol), 5.82 gram of tetraphenyl phosphonium bromide (13.9 mmol) and 6 ml sulfolane were introduced in a roundbottom flask. The flask was connected to a collecting flask, and the assembly was based in a kugelrohr apparatus. The reaction mixture was brought to 175° C. to initiate reactive distillation wherein the acrylic acid which is formed distills to the second flask. The reaction was carried out for 4 hours at atmospheric pressure under argon. The collecting flask was kept at 0° C. After the reaction the content of the reactor flask was analyzed, and found to contain 42 mg of acrylic acid (11% yield). The contents of the collecting flask were analyzed and found to contain 84 mg of acrylic acid (22% yield).

The invention claimed is:

1. Process for preparing acrylic acid and/or the ester of acrylic acid and lactic acid from a lactic acid oligomer or polymer, comprising the steps of
   a. bringing a reaction mixture comprising the lactic acid oligomer or polymer to reaction conditions to form acrylic acid and/or the ester of acrylic acid and lactic acid, the reacting mixture comprising a halide source selected from a bromide source and/or a chloride source and optionally an acid selected from the group of acids with a pKa of at most 2.0 and compounds which under reaction conditions decompose under the formation of an acid with a pKa of at most 2.0, with the reaction mixture comprising less than 1 wt.% of water, and
   b. keeping the reaction mixture under reaction conditions for a time sufficient to produce acrylic acid and/or the ester of acrylic acid and lactic acid.

2. The process according to claim 1, wherein the reaction mixture does not comprise an acid selected from the group of acids with a pKa of at most 2.0 and compounds which under reaction conditions decompose under the formation of an acid with a pKa of at most 2.0.

3. The process according to claim 2, wherein the reaction mixture comprises aluminum bromide and/or magnesium bromide as the halide source.

4. The process according to claim 1, wherein the reacting mixture comprises an acid selected from the group of acids with a pKa of at most 2.0 and compounds which under reaction conditions decompose under the formation of an acid with a pKa of at most 2.0.

5. The process according to claim 1, wherein the halide source comprises an organic halide salt.

6. The process according to claim 5, wherein the halide source is selected from the group of organophosphonium halide salts, imidazolium halide salts, pyridinium halide salts, organoammonium halide salts, and pyrrolidinium halide salts.

7. The process according to claim 1, wherein the halide source comprises an inorganic halide selected from the group of KBr, NaBr, CuBr, $FeBr_2$, $FeBr_3$, $NiBr_2$, LiBr, $MgBr_2$, $AlBr_3$, and $ZnBr_2$.

8. The process according to claim 1, wherein an acid is used with a pKa of at most 1.5.

9. The process according to claim 1, wherein a compound which under reaction conditions decomposes under the formation of an acid is used, the compound having a pKa of at most 1.5.

10. The process according to claim 1 wherein the water content of the reaction mixture is below 0.5 wt.%.

11. The process according to claim 1, wherein the molar ratio between the halogen source and the lactic acid oligomer or polymer, calculated as lactide, ranges from 10:1 to 0.1:1.

12. The process according to claim 1, wherein the molar ratio between the acid and the lactic acid oligomer or polymer, calculated as lactide, ranges from 0.01:1 to 1:1.

13. The process according to claim 1, wherein the reaction mixture further comprises a solvent.

14. The process according to claim 1, wherein the reaction temperature is from 20° C. to 400° C.

15. The process according to claim 1, which is operated in such a manner that the yield of acrylic acid is maximized.

16. The process according to claim 1, which is operated in such a manner that the yield of the ester of acrylic acid and lactic acid is maximized.

17. The process according to claim 1, wherein acrylic acid and/or the ester of acrylic acid with lactic acid is recovered from the reaction mixture during or after the reaction through distillation or extraction.

18. The process according to claim 17, which is carried out in the form of a reactive distillation process where acrylic acid is distilled from the reaction mixture during the reaction.

19. The process according to claim 1, wherein the halide source comprises an organic halide salt comprising a positively charged phosphorus or nitrogen atom and a negatively charged chloride or bromide ion.

20. The process according to claim 1, wherein an acid is used with a pKa of at most 1.0.

21. The process according to claim 1, wherein an acid is used that is organic acid.

22. The process according to claim 1, wherein a compound which under reaction conditions decomposes under the formation of an acid is used, the compound having a pKa of at most 1.0.

23. The process according to claim 1, wherein a compound which under reaction conditions decomposes under the formation of an acid is used, wherein the compound is selected from 2-bromopropionic acid and/or 3-bromopropionic acid.

24. The process according to claim 1 wherein the water content of the reaction mixture is below 0.1 wt.%.

25. The process according to claim 1, wherein the molar ratio between the halogen source and the lactic acid oligomer or polymer, calculated as lactide, ranges from 10:1 to 0.5:1.

26. The process according to claim 1, wherein the molar ratio between the acid and the lactic acid oligomer or polymer, calculated as lactide, ranges from 0.1:1 to 0.5:1.

27. The process according to claim 1, wherein the molar ratio between the acid and the lactic acid oligomer or polymer, calculated as lactide, ranges from 0.3:1 to 0.6:1.

28. The process according to claim 1, wherein the reaction mixture further comprises a polar aprotic solvent.

29. The process according to claim 1, wherein the reaction temperature is from 50° C. to 300° C.

30. The process according to claim 1, wherein the reaction temperature is from 100° C. to 250° C.

31. The process according to claim 1, wherein the reaction temperature is from 125° C. to 225° C.

* * * * *